(12) United States Patent
Klehr et al.

(10) Patent No.: US 7,864,311 B2
(45) Date of Patent: Jan. 4, 2011

(54) METHOD AND DEVICE FOR PRODUCING AND DETECTING A RAMAN SPECTRUM

(75) Inventors: Andreas Klehr, Berlin (DE); Bernd Sumpf, Berlin (DE); Martin Maiwald, Berlin (DE); Heinar Schmidt, Berlin (DE)

(73) Assignee: Forschungsverbund Berlin E.V., Berlin (DE)

(*) Notice: Subject to any disclaimer, the term of this patent is extended or adjusted under 35 U.S.C. 154(b) by 413 days.

(21) Appl. No.: 11/916,997

(22) PCT Filed: Jun. 13, 2006

(86) PCT No.: PCT/EP2006/063141

§ 371 (c)(1),
(2), (4) Date: Dec. 9, 2007

(87) PCT Pub. No.: WO2006/134103

PCT Pub. Date: Dec. 21, 2006

(65) Prior Publication Data

US 2008/0204715 A1 Aug. 28, 2008

(30) Foreign Application Priority Data

Jun. 14, 2005 (DE) .................... 10 2005 028 268

(51) Int. Cl.
*G01J 3/44* (2006.01)
(52) U.S. Cl. .................. 356/301; 356/303; 356/305
(58) Field of Classification Search .......... 356/301–305
See application file for complete search history.

(56) References Cited

U.S. PATENT DOCUMENTS 5,856,869 A 1/1999 Cooper et al.
5,946,090 A 8/1999 Tashiro et al.
6,697,665 B1 2/2004 Rava et al.
2005/0264808 A1* 12/2005 Wang .................... 356/328

FOREIGN PATENT DOCUMENTS

DE 692 31 614 T2 5/2001

(Continued)

*Primary Examiner*—Gregory J Toatley
*Assistant Examiner*—Tara S Pajoohi
(74) *Attorney, Agent, or Firm*—Perkins Coie LLP (57) ABSTRACT

The invention relates to a method and a device for producing and detecting a Raman spectrum. The problem addressed by the present invention is that of devising a method and a device for producing and detecting a Raman spectrum of a medium under investigation, whereby the Raman spectrum of a medium that is under investigation can be examined with a high degree of sensitivity while requiring relatively little equipment. The method is characterized by the coupling of excitation radiation into a medium (8) under investigation and the coupling of the electromagnetic radiation scattered by the medium (8) under investigation into a spectral optic system (10), a laser diode (1) for generating excitation radiation with at least two different wavelengths ($\lambda_1$, $\lambda_2$) being controlled with at least two different excitation conditions and at least one Raman spectrum (16, 17) being detected in each case from the scattered radiation at the different excitation wavelengths ($\lambda_1$, $\lambda_2$), and the Raman spectrum (20) of the medium (8) under investigation being determined from the at least two detected Raman spectra (16, 17), the two different excitation conditions for the laser diode (1) being adjusted by means of the electric current supplied to the laser diode (1).

20 Claims, 5 Drawing Sheets

FOREIGN PATENT DOCUMENTS

| WO | 99/35519 | A2 | 7/1999 |
| WO | 02/21087 | A1 | 3/2002 |
| WO | 2004/008121 | A2 | 1/2004 |
| WO | 2005/038437 | A2 | 4/2005 |
| WO | 2005/064314 | A1 | 7/2005 |

* cited by examiner

METHOD AND DEVICE FOR PRODUCING AND DETECTING A RAMAN SPECTRUM

FIELD OF THE INVENTION

The invention relates to a method and a device for producing an detecting a RAMAN scattering.

BACKGROUND

Raman spectroscopy has recently enjoyed widespread use in the fields of material science, chemical engineering, pharmacology, environmental technologies, chemical analysis, and process monitoring, mostly due to the development of less expensive semiconductor lasers. In many applications, the employed sensors are typically coupled to a spectrometer.

One general limitation for application of Raman spectroscopy in the aforementioned technical fields is that a fluorescence background or a broadband background scattering is frequently excited in addition to the desired Raman signals. Especially biological samples tend to fluoresce when the Raman effect is excited in the visible spectral range, which may completely obscure the Raman spectra. Although practically no fluorescence is produced when the Raman effect is excited with radiation in the far-infrared spectral range, the intensity of the Raman scattered radiation decreases with the fourth power of the absolute wave number, so that the optical spectrum analyzer must have a significantly higher sensitivity, which increases the complexity of the system.

Another problem is that with CCD detectors, the baseline has a characteristic structure, also referred to as fixed pattern. The fixed pattern is an unmovable interfering structure which is superimposed on the images of CCD cameras or CCD sensors. The fixed pattern masks the weak Raman signals (when using CCD-based detectors) and limits the attainable sensitivity. Conventional methods corrected this effect by requiring the measurement of a dark or null spectrum. However, even with this correction, the fix pattern can frequently not be eliminated sufficiently, because the measurement is performed in another intensity range and does not adequately take into consideration the physical nature of the fixed pattern.

Fluorescence suppression as well as background corrections have been investigated in Raman spectroscopy for many ways. For example, fluorescence in the spectrum can be eliminated by rapid gating, i.e., by taking advantage of the effect that the fluorescence response is slow compared to the Raman effect. However, this requires complex experimental setups with pulsed lasers, as disclosed, for example, by P. Matousek et al. "Fluorescence suppression in resonance Raman spectroscopy using a high-performance picosecond Kerr gate", J. Raman Spectroscopy 2001, 32, 983-988.

In addition, A. P. Sheve et al., Appl. Spectroscopy 1992, 46, 707, disclose that the fluorescence background can be corrected or even eliminated by using two laser wavelengths which are wavelength-shifted relative to one another. Sheve et al. use as a light source a Ti:Sapphire laser emitting at two frequency-shifted wavelengths produced with a diffractive element. However, disadvantageously, this setup is also rather complex.

Conventional methods and devices disadvantageously require complex equipment to attain adequate sensitivity for generating and detecting Raman spectra.

SUMMARY

It is an object of the present invention to provide a method and a device for generating and detecting a Raman spectrum of a medium to be investigated, so that the Raman spectrum of the medium to be investigated can be determined with high sensitivity and with a comparatively less complex measuring system. More particularly, the need to use of several excitation light sources is obviated. The method also allows in situ measurements with a high time resolution.

The method of the invention for generating and detecting a Raman spectrum of a medium to be investigated includes the following method steps:

producing electromagnetic excitation radiation with a laser diode, coupling the excitation radiation into the medium to be investigated, coupling the electromagnetic radiation scattered by the medium to be investigated into an optical spectrum analyzer for spectral analysis of the scattered radiation, wherein the laser diode for producing the excitation radiation at least two different wavelengths is controlled with at least two different excitation conditions, and wherein from the scattered radiation for each of the different excitation wavelengths at least two frequency-shifted Raman spectra are detected and the Raman spectrum of the medium to be investigated is computed from the at least two detected Raman spectra, and wherein the two different excitation conditions for the laser diode are set by the electric current applied to the laser diode.

The method of the invention has the particular advantage in that only a single laser diode is used, whereby the laser diode is capable of emission at two different wavelengths (preferably alternatingly) by the (preferably alternating) control of the laser diode with different excitation conditions (i.e., control of the laser diode at different current levels), so that for each of these two different (excitation) wavelengths a corresponding Raman spectrum can be detected, and a Raman spectrum for the medium to be investigated can be computed from the at least two obtained Raman spectra, wherein the fluorescence contribution can be computationally removed by detecting at least two frequency-shifted Raman spectra. It is also feasible to eliminate the fixed pattern and a device-specific spectral background (filter characteristic) when using CCD elements in the optical spectral analyzer. In this way, the system becomes less complex while retaining its high detection sensitivity, because only one laser diode is needed as excitation light source. According to the invention, the laser diode includes an internal frequency-selective element (preferably a grating, an etalon or a Mach-Zehnder interferometer). Another advantage of the invention is that the laser diode is controlled by the current level. Accordingly, rapid switching between the different excitation conditions is possible, so that rapidly changing processes can be monitored by Raman spectroscopy with high sensitivity, in spite of the reduced system complexity. Advantageously, the laser diode can be controlled much faster via the applied current level than by changing the temperature. Moreover, the apparatus becomes less complex because there is no longer a need for means for varying and/or controlling the temperature of the laser diode.

For elimination of the fixed pattern, the two wavelengths used for excitation should have adequate wavelength separation. A person skilled in the art would not expect that the necessary wavelength separation could be attained with a laser diode unless an external cavity is used. Disadvantageously, laser diodes with an external cavity are much less compact. Surprisingly, it has been observed that a laser diode with an internal frequency-selective element provides sufficient wavelength separation for eliminating the fixed pattern (by driving the laser diode at different current levels).

The linewidth (FWHM) of the laser diode is preferably less than 30 GHz, particularly preferred less than 3 GHz, particularly preferred less than 100 MHz, particularly preferred less than 10 MHz.

Use of a narrowband laser diode with a frequency-selective element can also eliminate the need for regular calibration (i.e., before and after each measurement) of the radiation emitted by the energized (with different excitation conditions) laser diode. A wavelength check need only be performed after extended periods of time. This significantly reduces the complexity of the equipment and the time requirements, so that the method of the invention can also be employed with conventional, lower-priced devices. A conventional light source which allows such real-time background suppression for Raman spectroscopy has in the past required significantly more complex equipment.

The employed laser diode is preferably monolithic and configured to be tunable over a predetermined wavelength range with a narrow emission wavelength.

Preferably, the laser diode is switched back and forth between the two current levels (or other excitation conditions) with a frequency greater than 0.1 Hz (in particular greater than 1 Hz). Alternatively, the excitation can also be non-periodic. The laser diode needs only to be controlled during a (preferably short) time interval with at least two different excitation conditions, so that the laser diode emits at least two wavelengths having sufficient wavelengths separation (preferably 0.5 nm). Preferably, the time interval is selected to be 60 seconds, particular preferred 10 seconds, particularly preferred 1 second, particularly preferred 0.1 second. The detector is preferably a line CCD. The optical spectrum analyzer is preferably a spectrograph with a line CCD. In addition, the laser diode can be driven with an excitation source (preferably a current source), whereby the output power of the excitation source is modulated. The excitation source is preferably modulated using a function generator, preferably a square-wave generator. The optical spectrum analyzer can also be connected to a data processing device for evaluating the measurement data received from the optical spectrum analyzer. For detecting the Raman spectra associated with the different excitation wavelengths (which are preferably coupled alternatingly into the medium), which is necessary for background suppression (computation), both the excitation source controlling the laser diode and the optical spectrum analyzer are gated. To this end, in addition to the excitation source, the optical spectrum analyzer and the data processing device are connected with the means for controlling the laser diode (modulator).

According to the invention, the device for generating and detecting a Raman spectrum includes an excitation light source, an optical spectrum analyzer and a data processing device, wherein the optical spectrum analyzer is connected to the data processing device, wherein the device further includes means for coupling the excitation radiation into the medium to be investigated and means for coupling the radiation scattered from the medium to be investigated into the optical spectrum analyzer, wherein the excitation light source is a laser diode with an internal frequency-selective element, wherein for producing different excitation wavelengths, the laser diode is connected with a current source via a modulator, wherein the optical spectrum analyzer and/or the data processing device are connected to the modulator.

In this way, the laser diode can emit narrowband radiation at two different wavelengths (preferably alternatingly, corresponding to the drive current), without requiring advance calibration of the individual wavelengths and/or of the laser diode. The device of the invention can be used to determine Raman spectra with high sensitivity (through elimination of fixed pattern and fluorescence contribution), wherein the device of the invention has a comparatively simple configuration (only a single excitation light source, no external cavity).

Preferably, the device of the invention includes optical filters, for example for eliminating the Rayleigh line.

Preferably, the optical spectrum analyzer and/or the data processing device are connected with the means for controlling the laser diode (e.g., modulator), because excitation at different wavelengths and detection of the scattered light can then occur simultaneously. This enables time-resolved observation, for example, of rapidly changing processes. The excitation conditions of the laser diode can also be switched at noticeably higher frequencies, for example at frequencies greater than 10 Hz (particularly preferred, greater than 30 Hz).

The modulator is preferably a function generator, particularly preferred is a square-wave generator. The means for coupling the excitation radiation into the medium to be investigated and the means for coupling the radiation backscattered from the medium to be investigated into the optical spectrum analyzer preferably include an optical fiber.

BRIEF DESCRIPTION OF THE DRAWINGS

The invention will now be described in more detail with reference to an exemplary embodiment.

DETAILED DESCRIPTION

Figure 1:
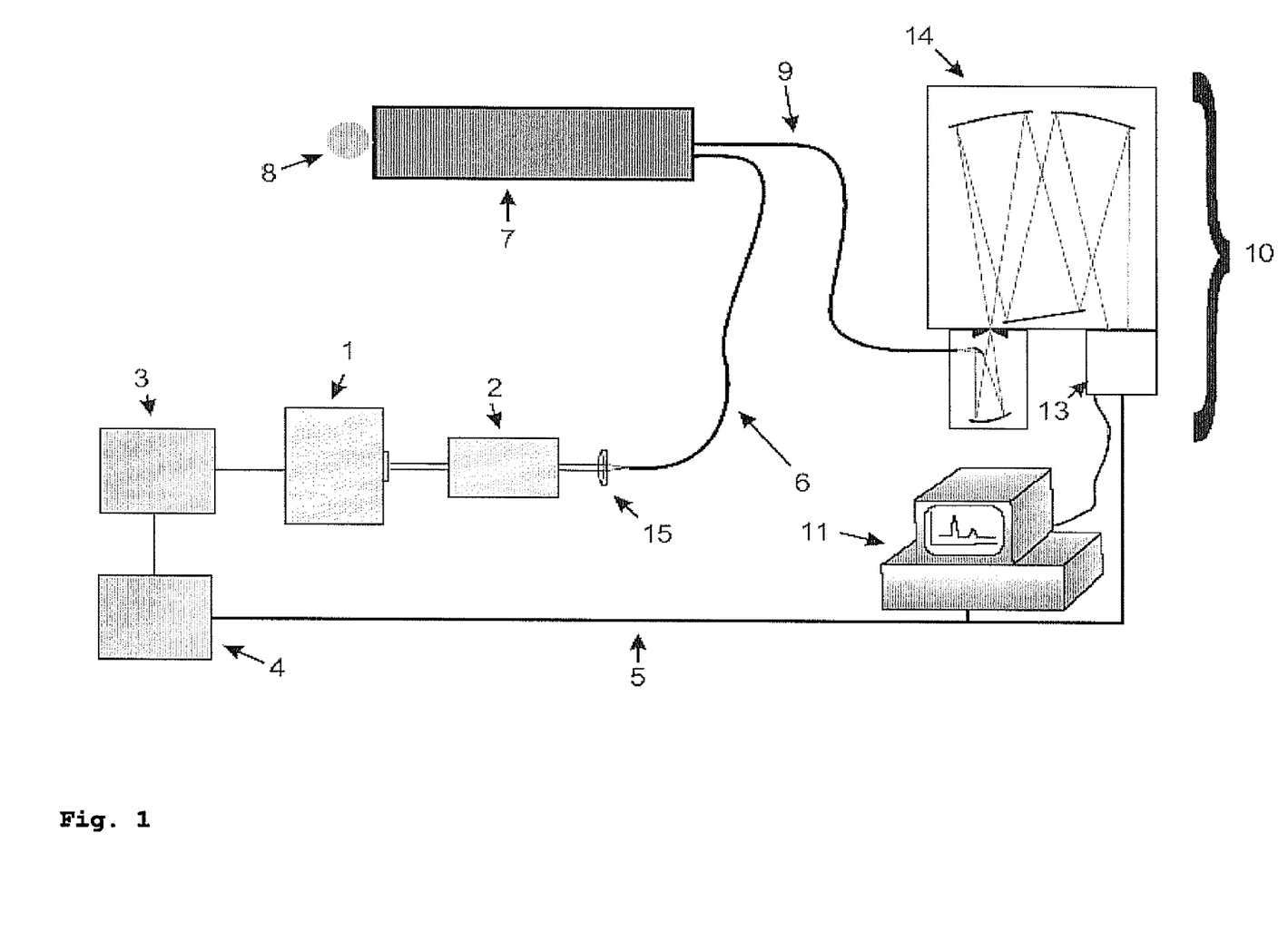
FIG. 1 shows schematically a device for generating and detecting a Raman spectrum according to the present invention.

FIG. 1 shows a device according to the invention for generating and detecting a Raman spectrum with a high sensitivity, with the device having comparatively less complexity. The laser diode 1 is connected to a DC current source 3, wherein the DC current source 3 is connected to a square-wave generator 4 which produces square pulses with a frequency of 0.1 Hz. The output power of the DC source 3 is modulated with the square pulses from the square-wave generator 4. The laser diode 1 is thereby driven alternatingly with two different electric currents (current levels). The laser diode 1 then emits in a narrow wavelength band at two different wavelengths, which according to the invention obviates the need to employ several excitation light sources. In the aforedescribed exemplary embodiment, the laser diode 1 is alternatingly driven at current levels of 150 mA and 250 mA with a switching frequency of 0.1 Hz.

Figure 2:
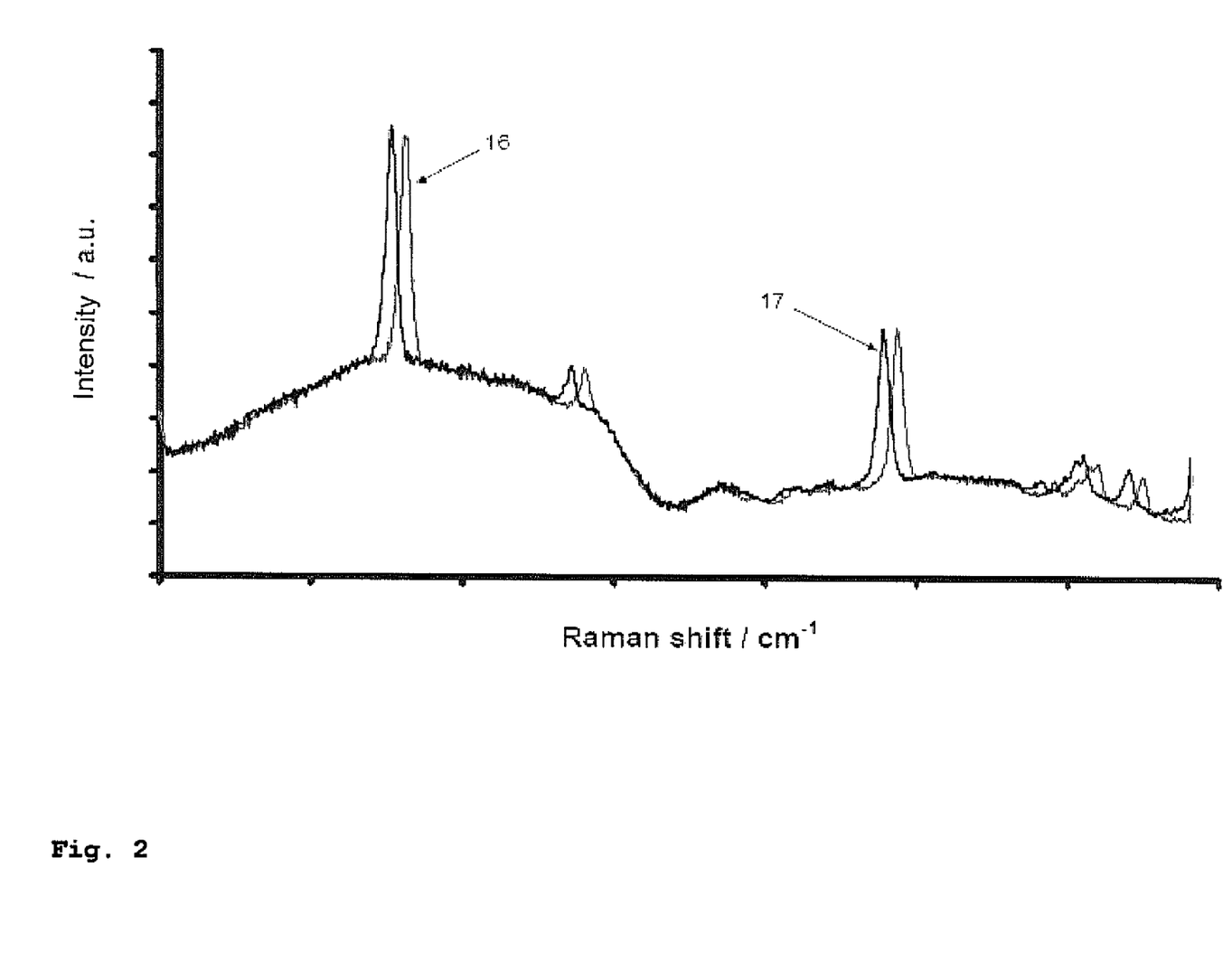
FIG. 2 shows the Raman spectrum of phenanthrene at two different excitation wavelengths $\lambda_1$ and $\lambda_2$.
Figure 3:
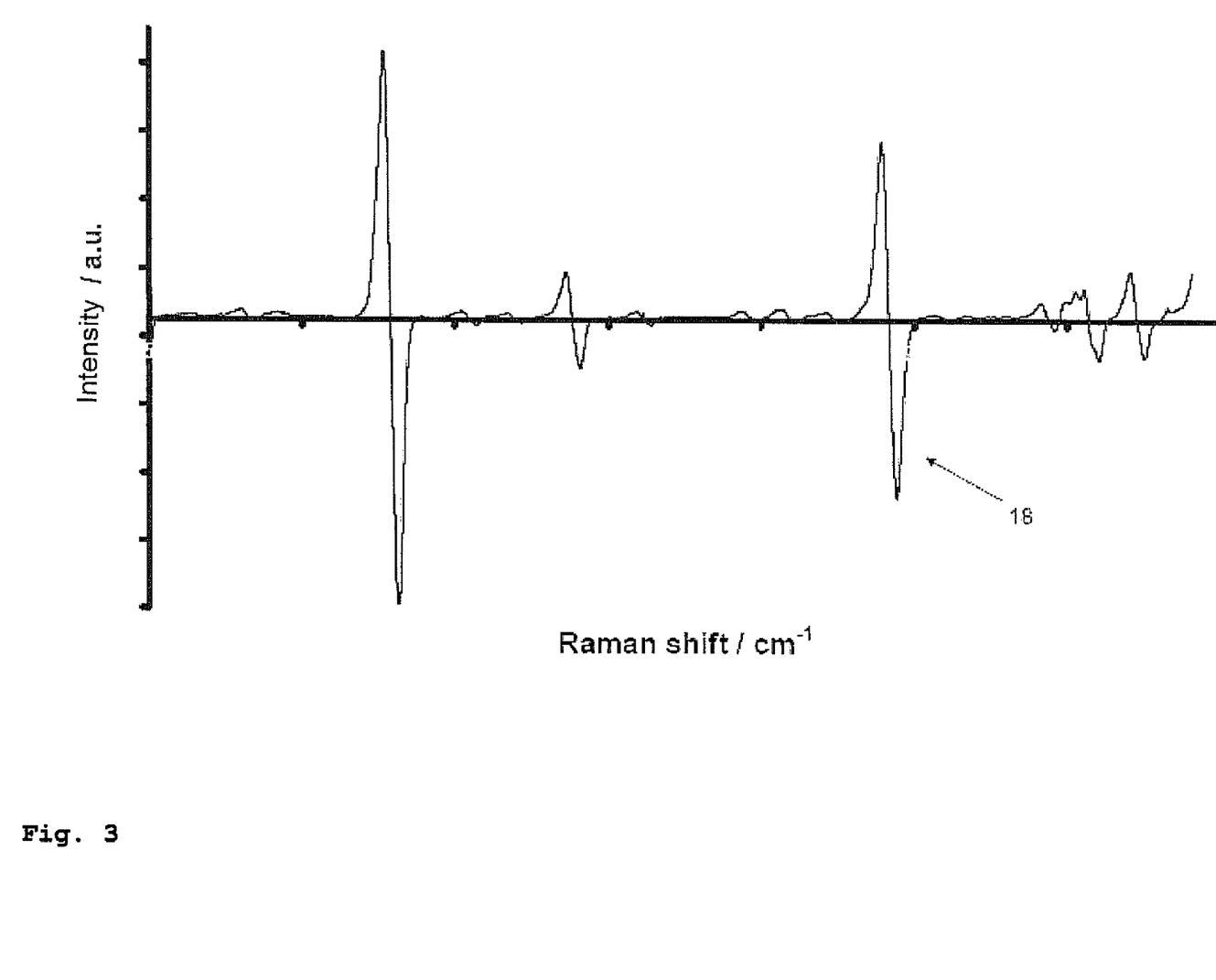
FIG. 3 shows the difference spectrum of the two Raman spectra of FIG. 2.
Figure 4:
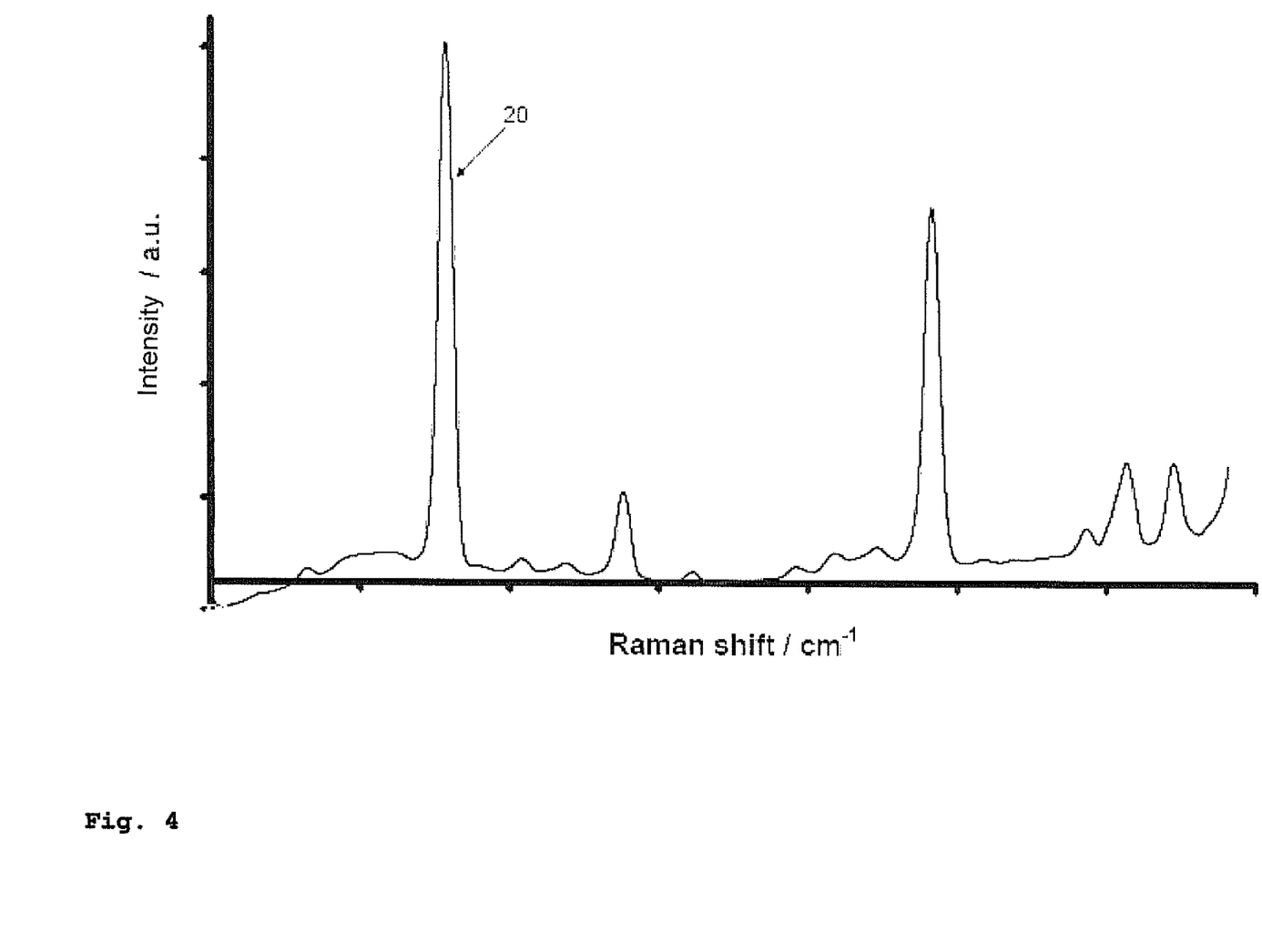
FIG. 4 is a reconstruction of the difference spectrum of FIG. 3.
Figure 5:
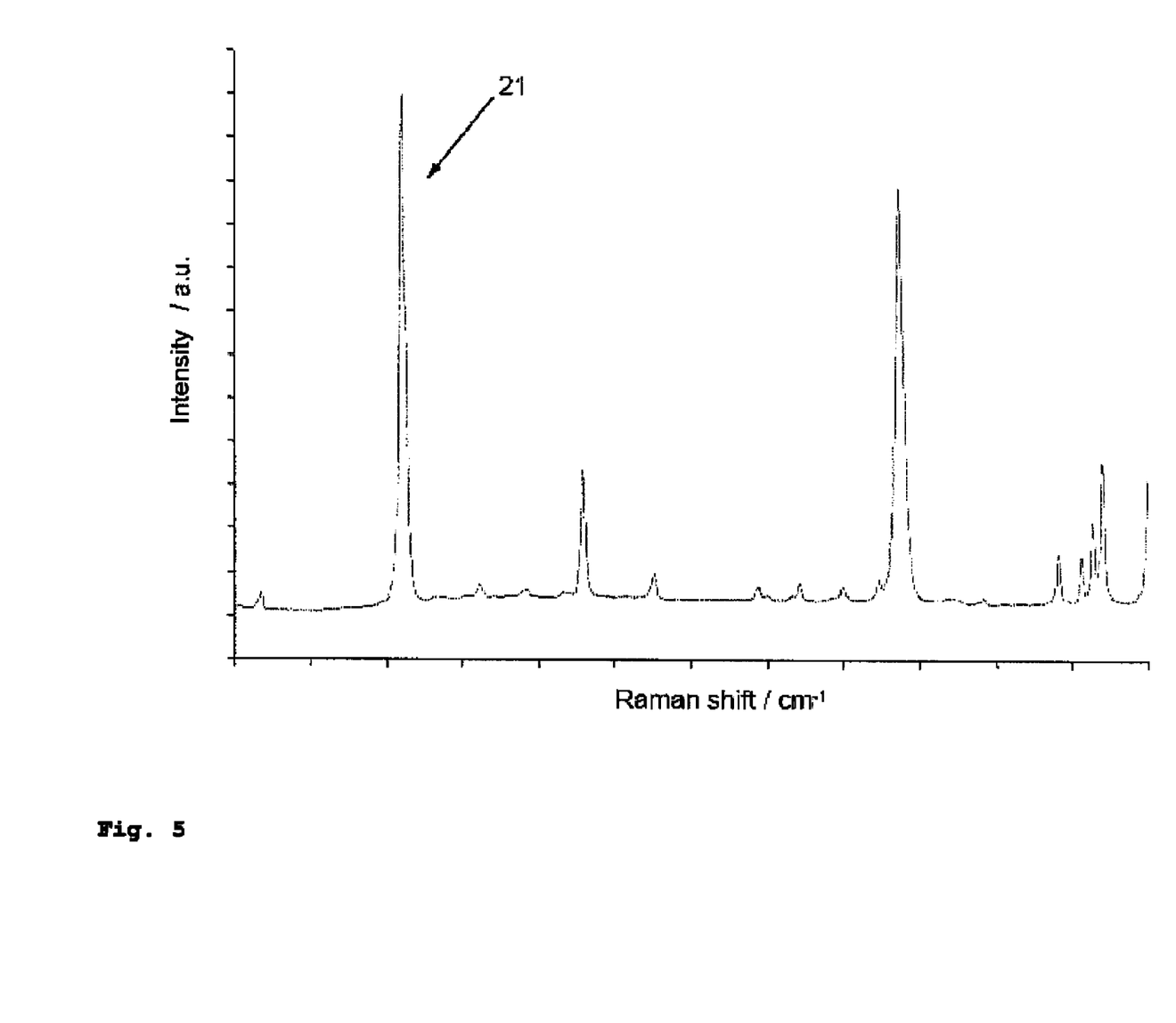
FIG. 5 shows a difference spectrum of phenanthrene.

Laser diode 1 then emits alternatingly at wavelengths of $\lambda_2=785.0$ nm and $\lambda_1=784.5$ nm. These wavelengths are then coupled into the optical fiber 6 via the optical isolator 2 and the lens system 15. The excitation radiation is coupled into the medium 8 to be investigated via the Raman measuring head 7. The medium 8 to be investigated is preferably arranged so as to prevent interfering light from entering the Raman measuring head 7, which may degrade the measurement. The excitation radiation is then partially scattered by the medium 8 to be investigated, and the scattered radiation of the medium 8 to be investigated is coupled via the Raman measuring head 7 and the optical fiber 9 into the optical spectrum analyzer 10, which consists of the spectrograph 14 and the line CCD 13. The spectrum 16 of the backscattered radiation at the excitation wavelength $\lambda_1$ and the spectrum 17 of the backscattered radiation at the excitation wavelength $\lambda_2$ are detected (see FIG. 2) in the optical spectrum analyzer 10, and the data for these spectra 16, 17 are transmitted to the data processing device 11. The line CCD 13 of the optical spectrum analyzer 10 and the data processing device 11 are (in addition to the laser diode 1) also connected (via the line 5) to the square-wave generator 4. (Alternatively, in addition to the laser diode 1, only the line CCD 13 may be connected to the square-wave generator 4). Control of the laser diode 1 and detection of the Raman spectra 16, 17 (at the corresponding two different excitation wavelengths $\lambda_1$ and $\lambda_2$) can then occur simultaneously. For example, the data processing device 11 for the two different excitation wavelength $\lambda_1$ and $\lambda_2$ may include Raman spectra 16, 17, facilitating calculation of a Raman spectrum in which the background (fixed pattern, fluorescence background) is computationally removed. To this end, first the difference spectrum 18 (see FIG. 2) is determined from the Raman spectra 16, 17, with the fixed pattern and background signals already removed. The difference spectrum can be mathematically reconstructed 20 from the difference spectrum 18 (see FIG. 4). A comparison with a reference spectrum (see FIG. 5) shows a good agreement between the Raman signals of the reconstructed spectrum and those of the reference spectrum.

LIST OF REFERENCE SYMBOLS

1 laser diode
2 optical isolator
3 DC source
4 square-wave generator
5 connection between square-wave generator and optical spectrum analyzer (line CCD)
6 optical fiber
7 Raman measuring head
8 medium (in a vessel)
9 optical fiber
10 optical spectrum analyzer
11 data processing device
13 line CCD
14 spectrograph
15 lens system
16 Raman spectrum of phenanthrene four and excitation wavelength $\lambda_1$
17 Raman spectrum of phenanthrene four and excitation wavelength $\lambda_2$
18 difference spectrum of 16 and 17
20 reconstructions of the difference spectrum
21 reference spectrum of phenanthrene

The invention claimed is:

1. Method for generating and detecting a Raman spectrum of a medium to be investigated, the method comprising the following steps:
    producing electromagnetic excitation radiation with a laser diode at least two different wavelengths by driving the electric current applied to the laser diode according to at least two different defined excitation conditions,
    coupling the excitation radiation into the medium to be investigated,
    coupling the electromagnetic radiation scattered by the medium to be investigated into an optical spectrum analyzer for spectral analysis of the scattered radiation,
    detecting at least one Raman spectrum from the scattered radiation for each of the different excitation wavelengths and
    determining the Raman spectrum of the medium to be investigated from the at least two detected Raman spectra,
    wherein
    the step of producing electromagnetic excitation radiation comprises using a laser diode with an internal frequency-selective element as an excitation light source,
    wherein the laser diode is driven in such a way that the laser diode alternately emits at least two defined wavelengths with a wavelengths separation of at least 0.5 nm, and
    wherein the electric current applied to the laser diode is driven alternately according to at least two different defined excitation conditions, wherein switching back and forth between the excitation conditions is performed with a frequency higher than 0.1 Hz.

2. Method according to claim 1, wherein the detection of the individual Raman spectra is synchronized with the alternating control of the laser diode.

3. Method according to claim 2, wherein for synchronizing the detection of the Raman spectra and the control of the laser diode, both the output power of an excitation source is modulated and a detector of the optical spectrum analyzer is synchronized.

4. Method according to claim 1, wherein the method further comprises the step of calibrating the laser diode before the excitation radiation is coupled into the medium to be investigated.

5. Method according to claim 1, wherein the frequency-selective element is implemented as a grating, an etalon, or a Mach-Zehnder interferometer.

6. Method according to claim 1, wherein the optical spectrum analyzer is implemented as a spectrograph with a line CCD.

7. Method according to claim 1, wherein the method further comprises amplification of the excitation radiation produced by the laser diode before being coupled into the medium to be investigated.

8. Method according to claim 1, wherein the radiation scattered by the medium to be investigated is coupled into the optical spectrum analyzer by an optical fiber.

9. Method according to claim 1, wherein the laser diode is driven by a current source, the output power of the current source being modulated.

10. Method according to claim 9, wherein a function generator is used for modulation.

11. Method according to claim 9, wherein each of the Raman spectra is detected within a time interval during which the magnitude of the current applied to the laser diode is constant.

12. Method according to claim 11, further comprising storing the individual Raman spectra by a data processing device.

13. Method according to claim 1, further comprising eliminating computationally a background and a fixed pattern from the at least two frequency-shifted detected Raman spectra.

14. Method according to claim 1, wherein the excitation radiation produced by the laser diode is coupled into the medium to be investigated by way of a Raman measuring head.

15. Device for generating excitation radiation and detecting a Raman spectrum of a medium to be investigated, comprising:
- an excitation light source,
- an optical spectrum analyzer and a data processing device, wherein the optical spectrum analyzer is connected to the data processing device,
- means for coupling the excitation radiation into the medium to be investigated,
- means for coupling the radiation scattered from the medium to be investigated into the optical spectrum analyzer,
- wherein the excitation light source is a laser diode with an internal frequency-selective element, and
- wherein for alternately producing different defined excitation wavelengths the laser diode is connected with a current source being modulated by a modulator, the optical spectrum analyzer and/or the data processing device being connected to the modulator,
- the modulator alternately modulates the current source, and wherein the frequency of alternation for the switching back and forth in the scope of the alternation is greater than 0.1 Hz.

16. Device according to claim 15, wherein the modulator is a function generator.

17. Device according to claim 15, wherein the modulator is a square-wave generator.

18. Device according to claim 15, wherein the means for couplings the excitation radiation into the medium to be investigated and the means for coupling the radiation scattered by the medium to be investigated into the optical spectrum analyzer comprise an optical fiber and a Raman measuring head.

19. Device according to claim 18, wherein an optical amplifier is arranged between the laser diode and the medium to be investigated.

20. Device according to claim 15, wherein the internal frequency-selective element is a grating, an etalon, or a Mach-Zehnder interferometer.

* * * * *